(12) United States Patent
Bailly et al.

(10) Patent No.: US 7,569,063 B2
(45) Date of Patent: Aug. 4, 2009

(54) INSTRUMENT FOR STORING AND DISPENSING A SURGICAL FASTENER

(75) Inventors: Pierre Bailly, Caluire (FR); Michel Therin, Lyons (FR); David Perdreaux, Saint Etienne sur Chalaronne (FR)

(73) Assignee: Sofradim Production SAS, Trevoux (FR)

( * ) Notice: Subject to any disclaimer, the term of this patent is extended or adjusted under 35 U.S.C. 154(b) by 530 days.

(21) Appl. No.: 11/581,128

(22) Filed: Oct. 13, 2006

(65) Prior Publication Data

US 2008/0087703 A1 Apr. 17, 2008

(51) Int. Cl.
*A61B 17/10* (2006.01)
(52) U.S. Cl. ...................................... 606/143
(58) Field of Classification Search ................ 606/143, 606/139, 142; 227/67, 68, 72
See application file for complete search history.

(56) References Cited

U.S. PATENT DOCUMENTS

| | | | |
|---|---|---|---|
| 4,448,194 A | 5/1984 | DiGiovanni et al. | |
| 4,669,473 A | 6/1987 | Richards et al. | |
| 4,696,300 A | 9/1987 | Anderson | |
| 4,736,746 A | 4/1988 | Anderson | |
| 5,171,249 A | 12/1992 | Stefanchik et al. | |
| 5,203,864 A | 4/1993 | Phillips | |
| 5,290,296 A | 3/1994 | Phillips | |
| 5,290,297 A | 3/1994 | Phillips | |
| 5,320,633 A | 6/1994 | Allen et al. | |
| 5,470,337 A | 11/1995 | Moss | |
| 5,601,571 A | 2/1997 | Moss | |
| 5,626,614 A | 5/1997 | Hart | |
| RE35,525 E | 6/1997 | Stefanchik et al. | |
| 5,643,319 A | 7/1997 | Green et al. | |
| 5,810,848 A | 9/1998 | Hayhurst | |
| 5,941,439 A | 8/1999 | Kammerer et al. | |
| 5,954,747 A | 9/1999 | Clark | |
| 5,997,552 A | 12/1999 | Person et al. | |
| 6,071,292 A | 6/2000 | Makower et al. | |
| 6,099,537 A | 8/2000 | Sugai et al. | |

(Continued)

FOREIGN PATENT DOCUMENTS

FR 2 876 020 4/2006

(Continued)

OTHER PUBLICATIONS

European Search Report from European Patent Application No. EP 06 29 1612 dated Feb. 27, 2007.

*Primary Examiner*—(Jackie) Tan-Uyen T. Ho
*Assistant Examiner*—Christina Lauer
(74) *Attorney, Agent, or Firm*—Carter, DeLuca, Farrell & Schmidt, LLP

(57) ABSTRACT

The device, designed to be fixed to the distal end of a fastener-positioning instrument, comprises a plane transverse distal end, a split first longitudinal channel and a second longitudinal channel, in which channels the anchoring bar and the stop bar of a fastener can slide, respectively. The device has a longitudinal bearing face that defines a half-space. The device further includes: a cam forming a stop/sliding surface for the distal end of the stop bar, in order to produce a pivoting movement of the stop bar; cams for the lateral splaying of the proximal part of the stop bar; and an escapement cam, allowing the lateral displacement of the distal part of the stop bar and its disengagement from the first cam.

17 Claims, 8 Drawing Sheets

U.S. PATENT DOCUMENTS

| | | | |
|---|---|---|---|
| 6,152,935 | A | 11/2000 | Kammerer et al. |
| 6,206,895 | B1 | 3/2001 | Levinson |
| 6,245,080 | B1 | 6/2001 | Levinson |
| 6,277,131 | B1 | 8/2001 | Kalikow |
| 6,319,263 | B1 | 11/2001 | Levinson |
| 6,352,541 | B1 | 3/2002 | Kienzle et al. |
| 6,398,796 | B2 | 6/2002 | Levinson |
| 6,425,900 | B1 | 7/2002 | Knodel et al. |
| 6,447,524 | B1 | 9/2002 | Knodel et al. |
| 6,457,625 | B1 | 10/2002 | Tormala et al. |
| 6,488,691 | B1 | 12/2002 | Carroll et al. |
| 6,491,707 | B2 | 12/2002 | Makower et al. |
| 6,551,333 | B2 | 4/2003 | Kuhns et al. |
| 6,572,626 | B1 | 6/2003 | Knodel et al. |
| 6,596,014 | B2 | 7/2003 | Levinson et al. |
| 6,613,059 | B2 | 9/2003 | Schaller et al. |
| 6,656,182 | B1 | 12/2003 | Hayhurst |
| 6,692,506 | B1 | 2/2004 | Ory et al. |
| 6,730,112 | B2 | 5/2004 | Levinson |
| 6,752,307 | B2 | 6/2004 | Raymond |
| 6,779,701 | B2 * | 8/2004 | Bailly et al. ............. 227/176.1 |
| 6,837,413 | B1 | 1/2005 | Raymond et al. |
| 6,837,895 | B2 | 1/2005 | Mayenberger |
| 6,849,079 | B1 | 2/2005 | Blake, III et al. |
| 2001/0010005 | A1 | 7/2001 | Kammerer et al. |
| 2005/0187565 | A1 | 8/2005 | Baker et al. |

FOREIGN PATENT DOCUMENTS

| | | |
|---|---|---|
| WO | WO 87/01270 | 3/1987 |
| WO | WO 98/51179 | 11/1998 |
| WO | WO 99/39645 | 12/1999 |
| WO | WO 00/67644 | 11/2000 |
| WO | WO 03/075773 A | 9/2003 |

* cited by examiner

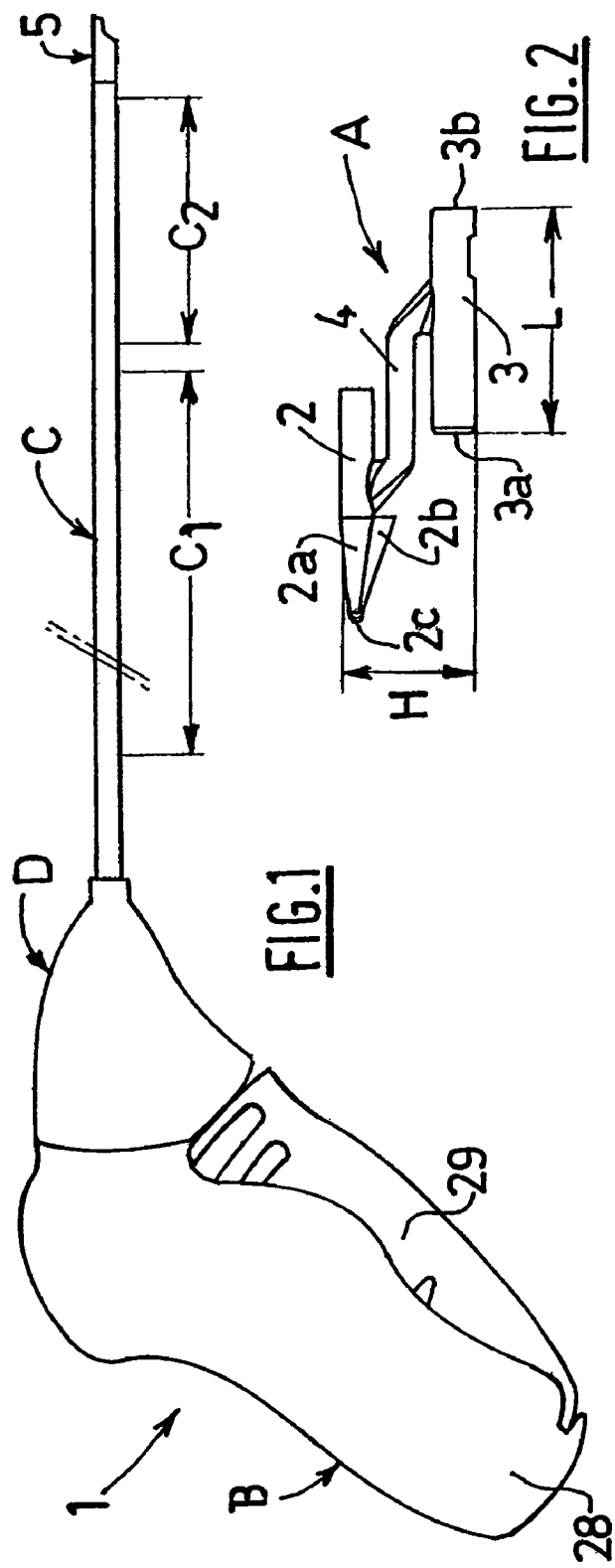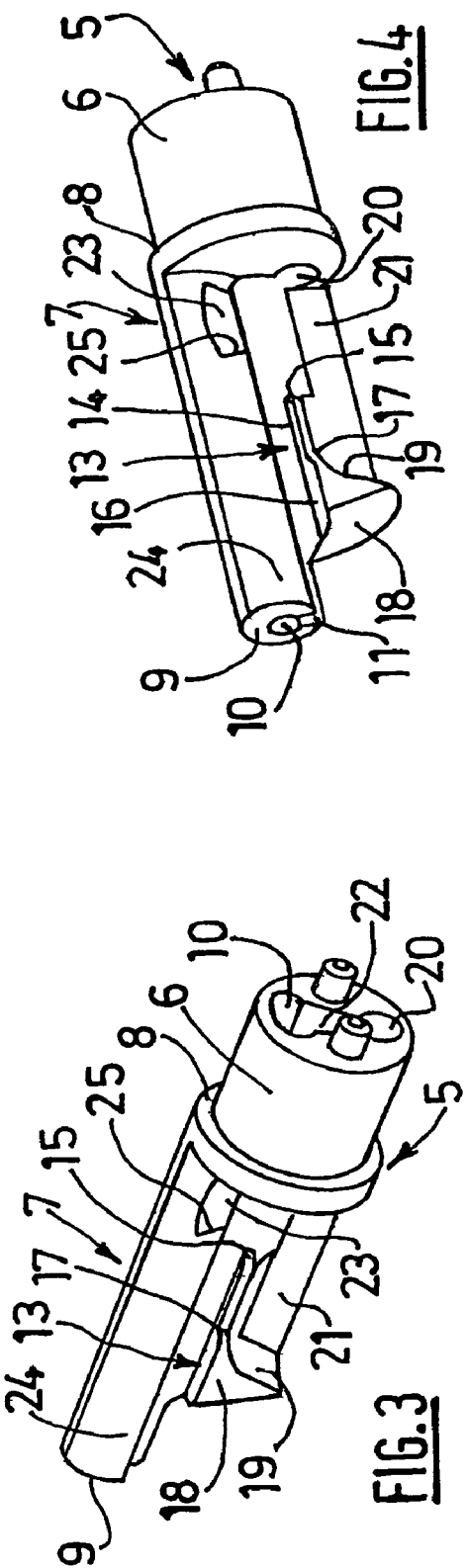

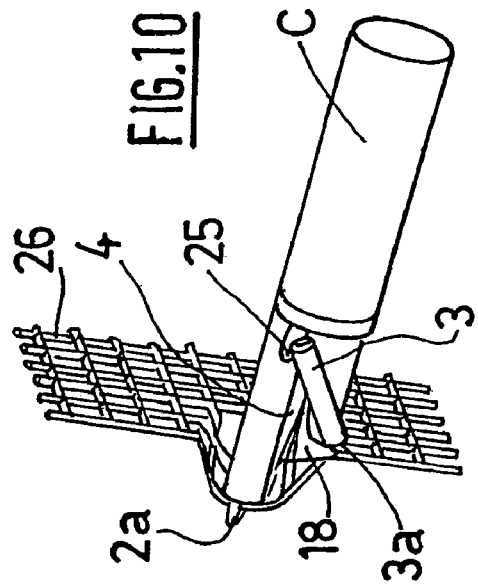
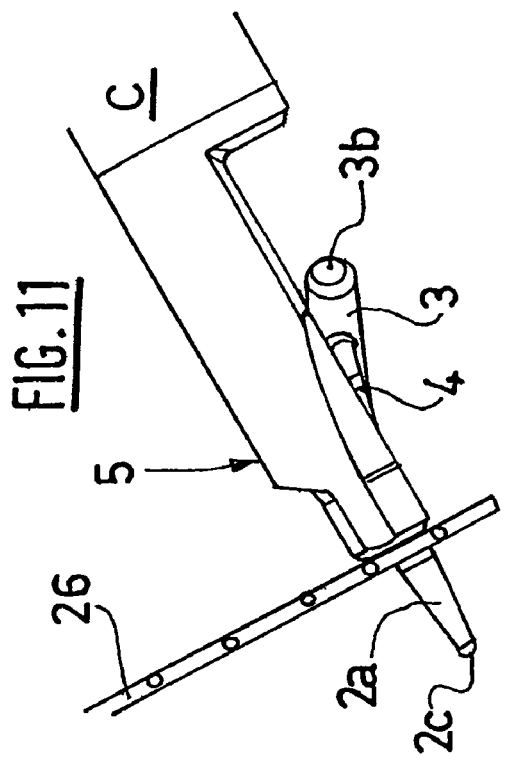
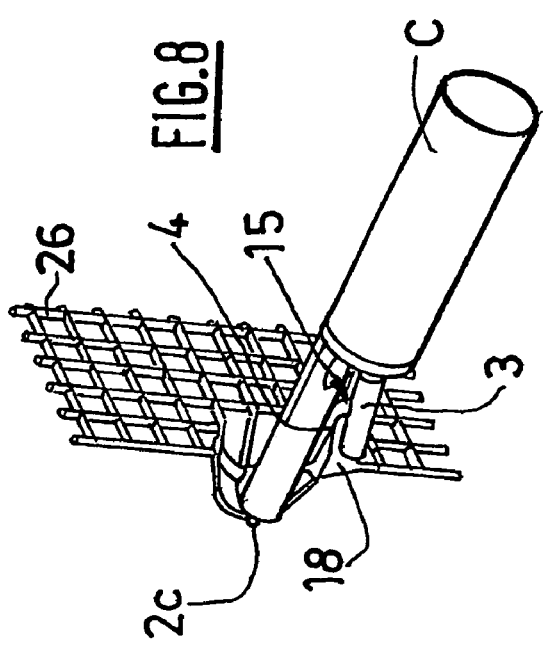
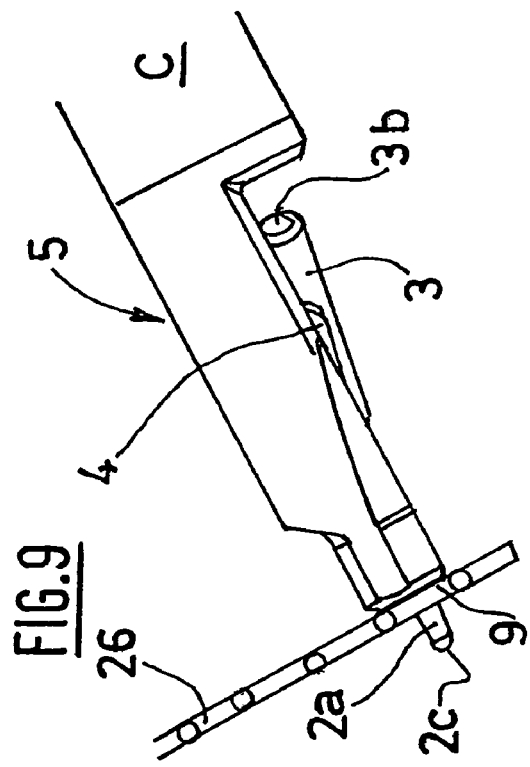

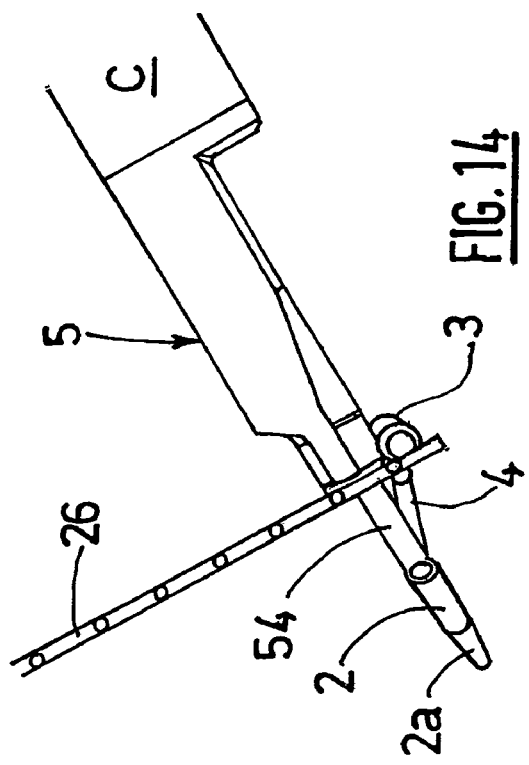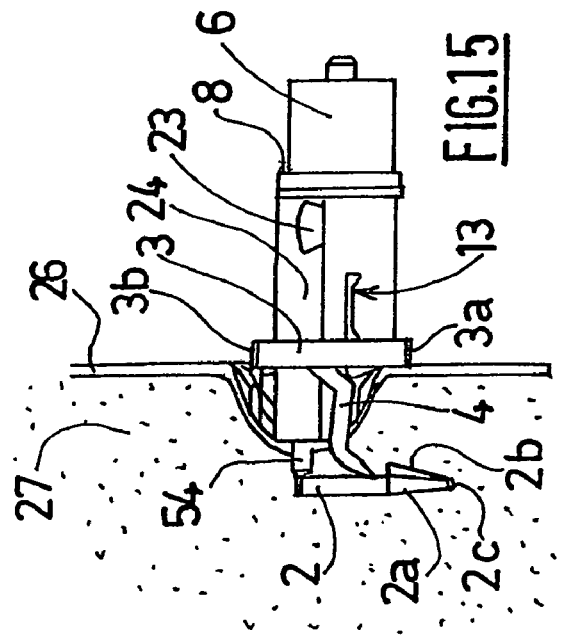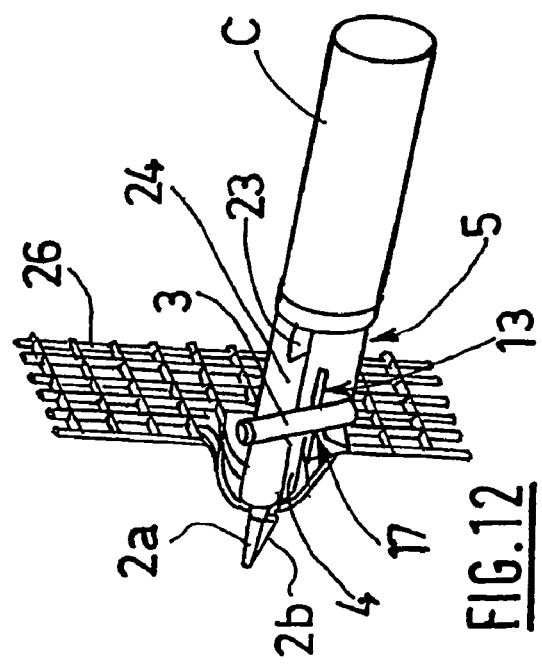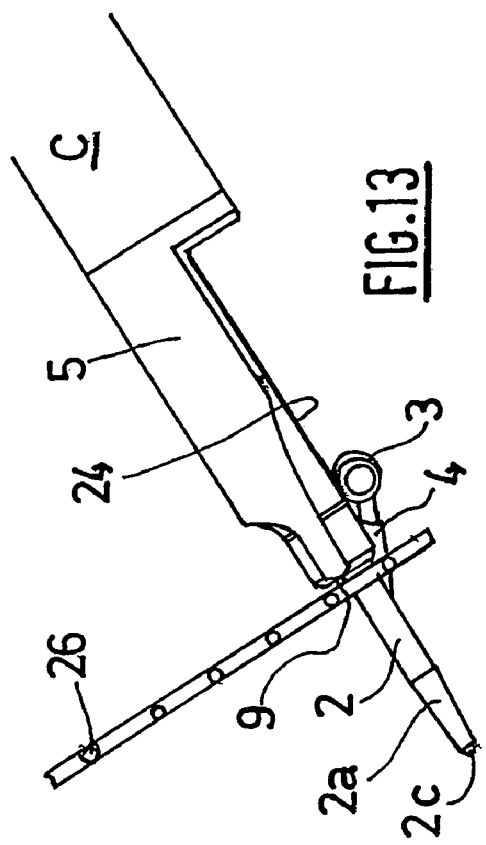

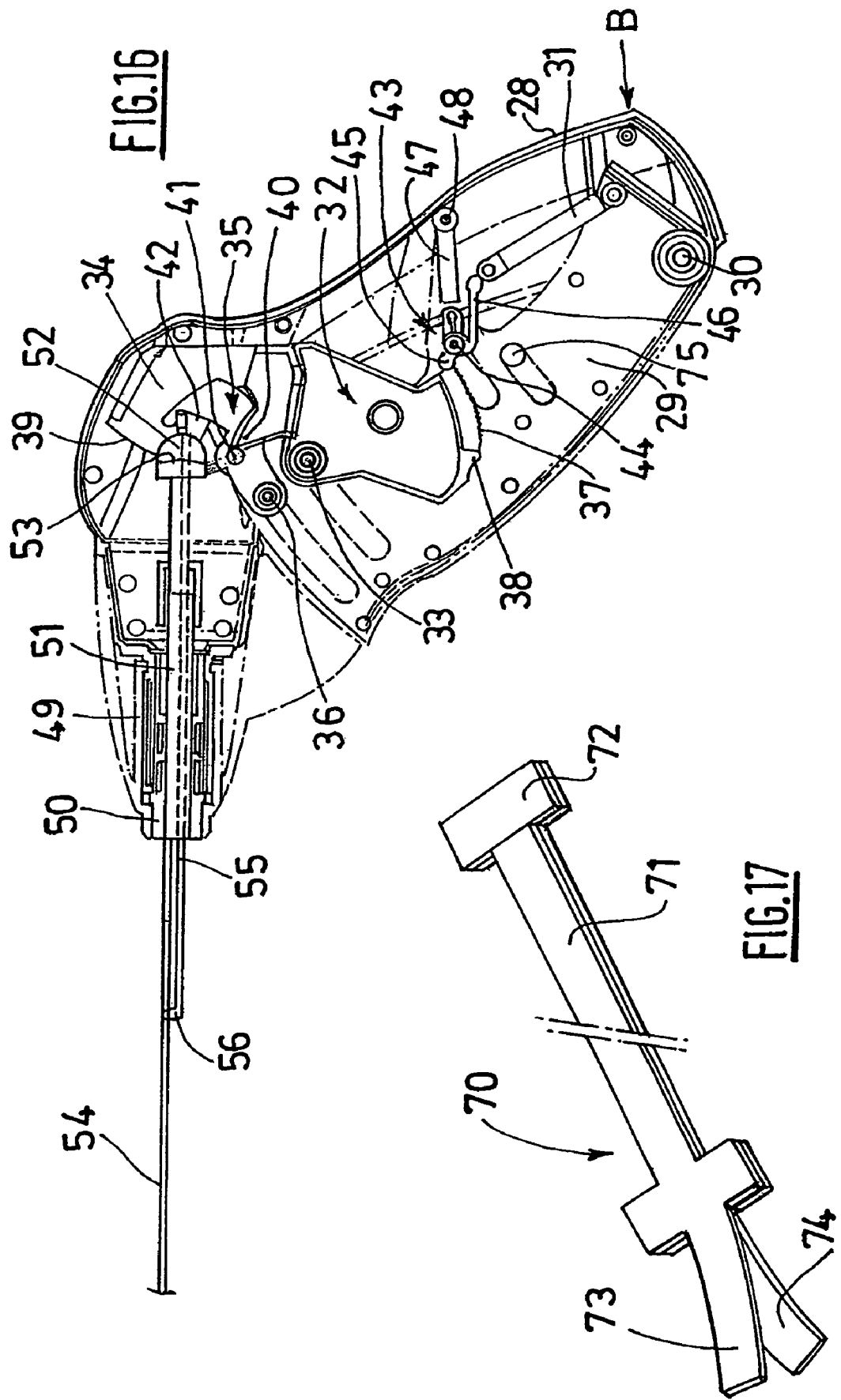

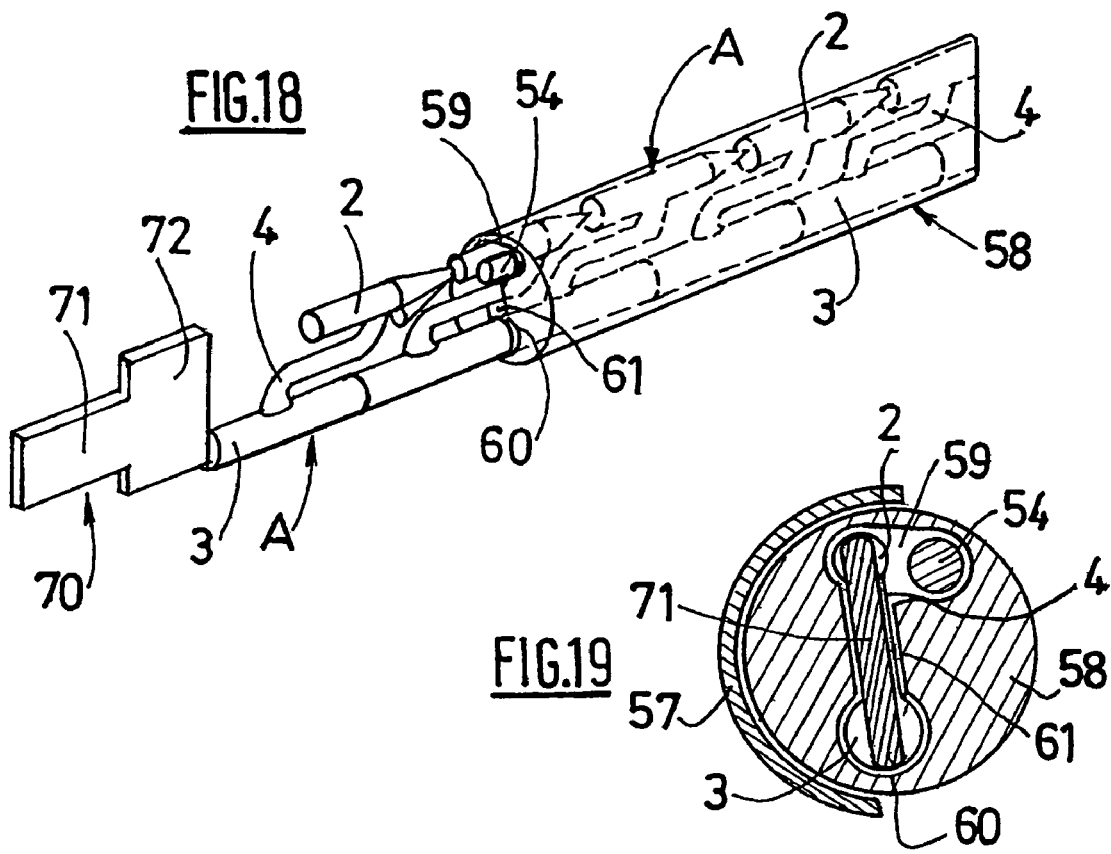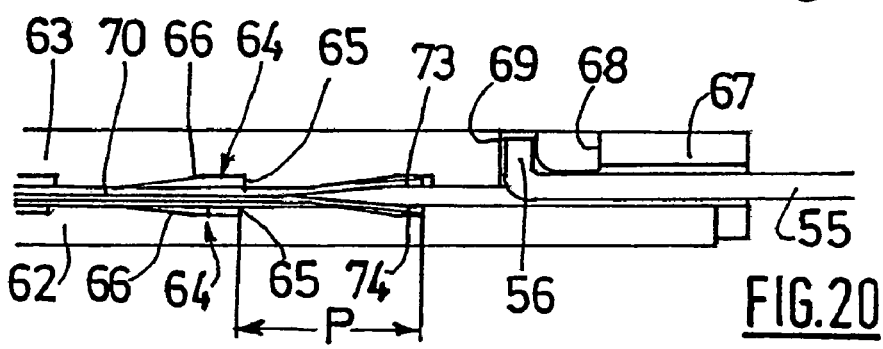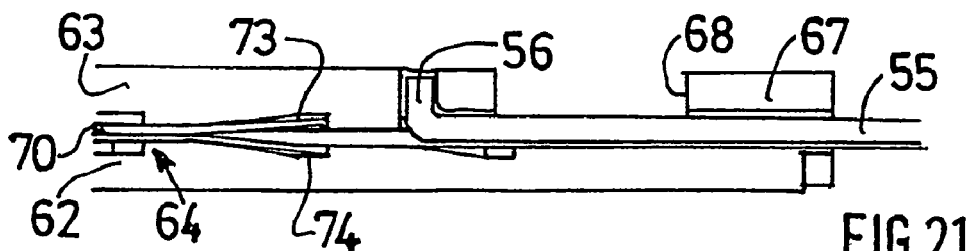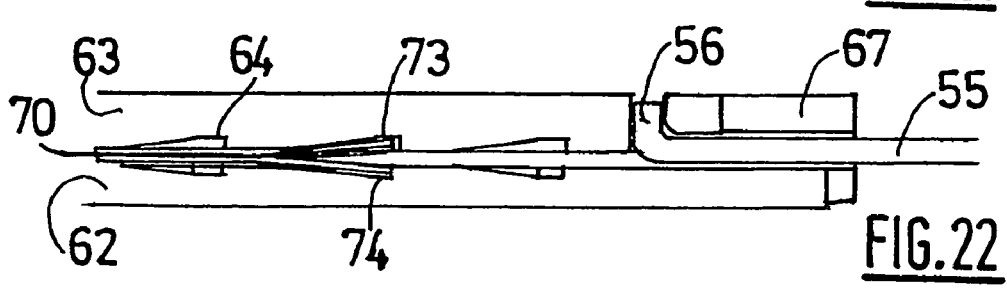

INSTRUMENT FOR STORING AND DISPENSING A SURGICAL FASTENER

The present disclosure relates to a device for deploying and ejecting a recumbent I-shaped surgical fastener, the fastener comprising an anchoring bar, a stop bar and a linking strip. The device is configured for attachment at a distal end of an instrument for storing, dispensing and positioning such fasteners.

WO 03/075773 already discloses an instrument for dispensing and positioning surgical fasteners with the aim of fastening the fabric of a prosthesis to human tissue, for example the abdominal wall of a patient. In that document, the fasteners are positioned by means of a hollow, bevelled needle, which passes through the prosthesis and flesh.

Also disclosed, in document FR 2 876 020, is another instrument for dispensing and positioning surgical fasteners, in which the needle is replaced with an ejection guide, the distal end of which is straight and not bevelled. Penetration of a fastener into flesh is ensured by the shape of the distal part of the anchoring bar, namely a conical shape terminating in a hemispherical shape.

At rest the ejection guide is housed in the tubular body of the instrument and the positioning of the fasteners is accompanied by the translational movement of the ejection guide towards the distal end of the instrument, the length of the projecting part of the ejection guide at the moment of ejection being equal to 3 mm or less. The fasteners, initially in the form of a recumbent I, are unfolded inside the ejection guide, therefore inside the tubular body of the instrument, and it is only once the stop bar is straightened up that it leaves the tubular body.

Such an instrument may be used by introducing the tubular body into a trocar. The tendency is to use trocars having the smallest diameter possible, for example around 5 mm. The diameter of the tubular body is therefore reduced accordingly. It follows that the fasteners, which must have dimensions sufficient to exert their retention function on the prosthesis in human tissue, are forced, when they are being stored in this tubular body, to be even more folded-up. Their deployment is therefore more tricky and, in addition, it cannot take place in the tubular body, the diameter of which is smaller than the size of an unfolded fastener.

One object of the present disclosure is to provide a device for deploying and ejecting a recumbent I-shaped surgical fastener, which allows satisfactory deployment of the fastener even when it is stored in a small-diameter tubular body.

For this purpose, and according to a first aspect, the disclosure relates to a device for deploying and ejecting a recumbent I-shaped surgical fastener. The fastener comprises an anchoring bar, a stop bar and a linking strip. The device is positioned adjacent a distal end of the instrument and is intended to be fixed to the distal end of an instrument for storing, dispensing and positioning such fasteners, the device having a longitudinal axis and a distal end that lies in a plane approximately orthogonal to the longitudinal axis and includes a first longitudinal channel emerging at the proximal and distal ends of the device, in which the anchoring bar of a fastener can slide longitudinally up to a point where it is ejected at the distal end of the device, the first channel having a longitudinal slot intended for passage of the linking strip of said fastener during said sliding.

According to a general definition of the disclosure, the device has an approximately longitudinal bearing face that defines an open half-space. The device further includes:
- a second longitudinal channel in which the stop bar can slide towards the distal end of the device, the second channel lying approximately in the same plane as the first channel and the slot of the first channel, emerging at the proximal end of the device and extending into the open half-space against the bearing face;
- a first cam that closes off the distal end of the second channel and designed to form a stop surface for the distal end of the stop bar and to allow sliding from said distal end in the opposite direction to the first channel so as to produce a pivoting movement of the stop bar;
- at least one approximately transverse splaying cam, located proximal to the first cam, capable of cooperating with the linking strip and/or the stop bar in order to cause a lateral splaying movement of the proximal part of the stop bar away from the bearing face; and
- an approximately transverse escapement cam, located between the first cam and the one or more splaying cams, capable of cooperating with the distal part of the stop bar in order to allow lateral displacement of the distal part of the stop bar away from the bearing face, and its disengagement from the first cam.

When the deployment of the ejection device is fixed to the distal end of the instrument, the open half-space lies outside the tubular body of this instrument. It is in this half-space that the deployment of the fastener takes place, which is therefore not impeded by the tubular body of restricted dimensions.

This arrangement, in combination with the fact that the first cam is shaped so as to allow the distal end of the stop bar to slide away from the first channel, allows the stop bar to pass beyond the diameter of the deployment/ejection device, both downwards (away from the first channel) and upwards. This was not possible with the instruments of the prior art, in which there was only a means of blocking the distal end of the stop bar, which did not allow the latter to slide downwards—it was therefore necessary for the tubular body to have a large diameter, especially so as to permit the stop bar to pivot without the proximal end of the latter being blocked in this movement by butting against the internal face of the tubular body.

Moreover, owing to the fact that the distal end of the device lies in a plane approximately orthogonal to the longitudinal axis, the device is capable of dispensing the fasteners with minimum trauma.

The first cam may generally lie in a plane orthogonal to the bearing face and is inclined, on going away from the first channel, from the proximal end of the device towards the distal end.

Advantageously, the first cam has, seen in cross section in a longitudinal plane orthogonal to the bearing face, a concave shape. It thus forms a gutter that allows the distal end of the stop bar to be guided during its sliding movement, while preventing it from escaping.

In one embodiment, the device may comprise two splaying cams designed to cause two sequenced lateral splaying movements of the proximal part of the stop bar.

The device may also include a longitudinal rib projecting approximately at right angles from the bearing face. The proximal face of said rib forms a first ramp constituting a splaying cam. Furthermore, the rib may have a distal part of greater height than its proximal part, the proximal face of the distal part of the rib forming a second ramp which, located distal of the first ramp, constitutes the escapement cam.

In one embodiment, the device includes a cavity formed in the bearing face, in line with the first channel, proximal of the proximal face of the rib, the distal face of which constitutes a subsequent splaying cam.

Moreover, the first channel may have a proximal part of larger transverse dimension than the distal part, a side wall of the proximal part of the first channel forming a ramp over which the distal end of the anchoring bar of a fastener can slide in order to cause the lateral displacement of said anchoring bar towards the distal part of the first channel.

In embodiments, the device may have an approximately cylindrical shape, with a diameter less than 6 mm. It may further include a proximal cylindrical appendage of smaller diameter, intended to be inserted into the distal end part of an instrument for storing, dispensing and positioning surgical fasteners.

In one embodiment, the distal end of the device includes a transverse wall substantially flanking the distal outlet of the first channel. The material added by the presence of this transverse wall provides further protection of the device and minimizes the thrust of the distal end of the device against human tissue when the fastener is being positioned.

According to a second aspect, the disclosure relates to an instrument for storing, dispensing and positioning recumbent I-shaped surgical fasteners. The fasteners include an anchoring rod, a stop bar and a linking strip. The instrument includes a gripping means provided with an actuator that can move on a body between a pushed-out position and a pushed-in position. The instrument further includes an elongate tubular body in which fasteners are stored longitudinally one behind another. The tubular body is fixed to the body of the gripping means and further includes a device for deploying and ejecting a fastener as described above. The device is fixed to the distal end of the tubular body so that the open half-space is located outside the tubular body.

In one embodiment the instrument includes:
  a stationary component housed in the tubular body and a moving component housed in the tubular body so that it can be moved in longitudinal translation with respect to the stationary component by means of an advancing rod that can be actuated by the actuator. The stationary and moving components are positioned along a longitudinal face and each having notches provided in said longitudinal face, with a pitch corresponding to the length of the stop bar of a fastener; and
  a slide placed between the longitudinal faces of the stationary and moving components, having an approximately planar main part, a distal part that bears against the proximal end of the stop bar of the proximal most fastener and, in its proximal part, a first resilient tongue projecting towards the moving component and a second resilient tongue projecting towards the stationary component, each capable of being engaged in a corresponding notch. The geometry of the notches is designed so that the displacement of the moving component with respect to the stationary component towards the distal end of the instrument causes, by means of the first tongue engaged in a notch of the moving component, the displacement of the slide in the same direction, until the second tongue of the slide is engaged in a notch of the stationary component. The cooperation between the second tongue and a notch of the stationary component prevents the slide from returning towards the proximal end of the instrument when the moving component is displaced relative to the stationary component towards the proximal end of the instrument.

The stationary and moving components may have the form of semicylinders, the moving component including a radial orifice into which the curved end of the advancing rod is inserted.

According to one embodiment, the instrument includes a magazine for storing the fasteners. The magazine includes a first longitudinal housing that receives the aligned anchoring bars of the fasteners and, contiguously, an ejection rod that can be actuated by the actuator. The magazine further includes a second longitudinal housing that receives the aligned stop bars of the fasteners, and a third housing, which joins the first and second housings, is configured for passage of the linking strips.

The gripping means may include:
  first and second levers that can be moved, by pushing in the actuator, between a proximal rest position and a distal end position. Movement to the end position causes longitudinal displacement in the distal direction of a rod for ejecting the distalmost fastener out of the deployment/ejection device; and of a rod for advancing the fasteners in the tubular body, respectively;
  a member mounted so as to pivot about a pin attached to the body of the gripping means, which member includes a tooth capable of cooperating with a rack formed on one of the levers during displacement of the actuator; and
  a flexible return means, one end of which is connected to the pivoting member and the other end of which is connected to the body of the gripping means. The elastic return means and the profile of the tooth and the rack being designed so that:
  when the actuator is pushed in as far as an intermediate pushed-in position, the elastic return means urges the pivoting member towards a position such that the cooperation between the tooth of the pivoting member and the rack of the lever prevents the actuator from returning to the pushed-out position from said intermediate pushed-in position; and
  after the levers have reached their distalmost end position, upon releasing the actuator as far as an intermediate release position, the flexible return means urges the pivoting member towards a position such that the cooperation between the tooth of the pivoting member and the rack of the lever prevents the actuator from being pushed in from said intermediate release position.

A double non-return system may thus advantageously be obtained.

Advantageously, the rack of the lever includes, at its distal end, a tooth of larger size and the pivoting member includes, a finger on one side, and a tab on the other side. The rack cooperates with a stop attached to the body of the gripping means when the finger comes into contact with the larger tooth. Thus when the actuator has been pushed in the tab of the pivoting member in contact with the stop must flex in order for the finger to pass beyond the larger tooth. When the actuator is pushed in, the user therefore receives a tactile indication that he has reached the fully pushed-in position of the actuator, and therefore that the fastener has been suitably ejected.

The present disclosure also relates to a recumbent I-shaped surgical fastener having an anchoring bar, a stop bar and a linking strip. The distal part of the anchoring bar has approximately the shape of a truncated cone with the external slope of the cone being more accentuated than the internal slope turned towards the stop bar.

The fastener is deployed from an internal storage position, in which it has a recumbent "I" shape, to an operating position, in which it tends towards an upright "I" configuration. The accentuation of the external slope of the cone allows the anchoring bar to pivot more naturally towards the stop bar when the fastener is being deployed in tissue.

The distal end of the device has a hemispherical shape. Thus, the fastener penetrates more easily into tissue during its installation.

One embodiment of the disclosure will now be described with reference to the appended figures, in which:

FIG. 1 is a side view of an instrument for storing, dispensing and positioning surgical fasteners;

FIG. 2 is a side view of a recumbent I-shaped surgical fastener in the storage position;

FIGS. 3 and 4 are perspective views, from the rear and front respectively, of a device for deploying and ejecting a surgical fastener;

FIGS. 6 to 15 illustrate successive steps in the deployment and ejection of a fastener;

FIG. 16 is a side view showing the mechanism of the instrument, housed inside the gripping means;

FIG. 17 is a perspective view of the slide in the tubular body for advancing the fasteners;

FIG. 18 is a partial schematic view of a series of fasteners that are stored in a magazine, and of the distal end of the slide of FIG. 17;

FIG. 19 is a partial cross-sectional view of the tubular body in the region that receives the magazine;

FIGS. 20 to 22 are schematic representations in a lateral sectional view of the fastener-advancing system;

Figure 5:
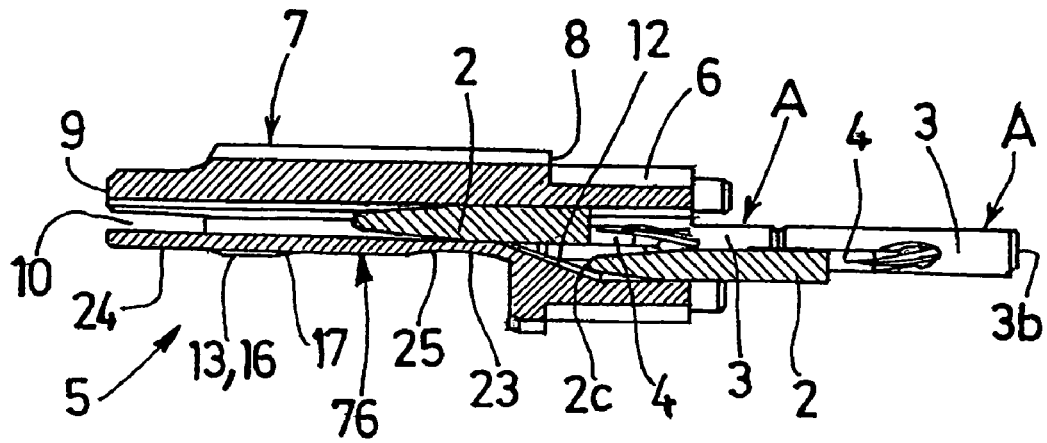
FIG. 5 is a sectional view of the deployment/ejection device, in a longitudinal plane.
Figure 6:
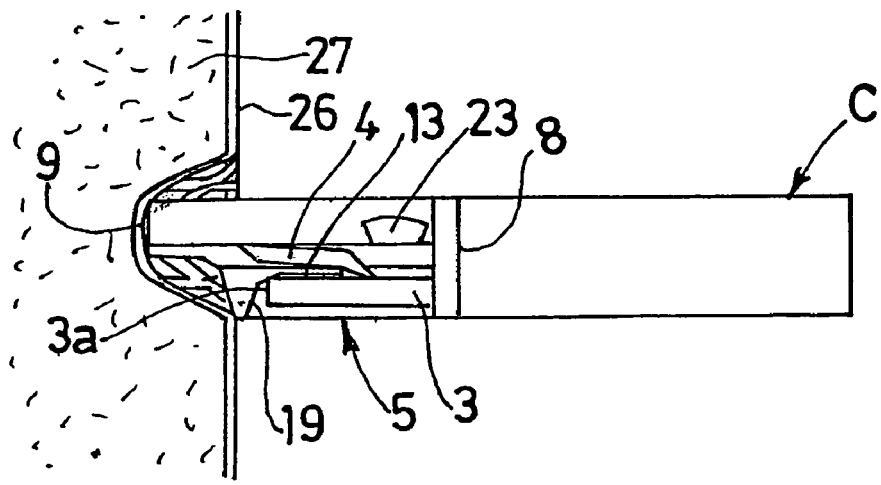
Figure 7:
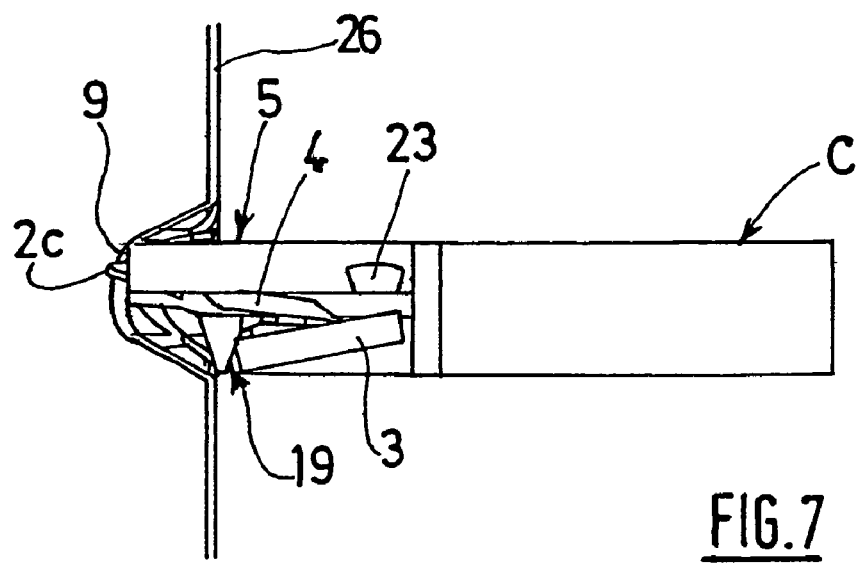

The instrument 1 shown in FIG. 1 is designed to dispense fasteners A which have, as shown in FIG. 2, the general shape of a recumbent "I" and are composed of two parallel bars, namely an anchoring bar 2 and a stop bar 3, joined together by a linking strip 4. The fastener A is made of plastic, especially a biocompatible and preferably bioresorbable material.

The distal part 2a of the anchoring bar 2 has a conical shape. This distal part 2a may include a notch 2b projecting towards the stop bar 3 in order to protect the anchoring bar 2/linking strip 4 intersection, which is stressed at the moment when the fastener A is ejected and positioned. Furthermore, the distal end 2c of the anchoring bar 2 has a hemispherical shape.

The term "proximal" relates to a location closer to the user of the instrument 1, while the term "distal" relates to a location further from the user.

The stop bar 3 has a distal end 3a and a proximal end 3b, and has a length L.

The linking strip 4 is joined to the anchoring bar 2, approximately at the center of the latter, and is joined to the stop bar 3 in a region close to the center of the stop bar 3, but slightly offset towards its proximal end 3b. In one embodiment, the length L of the anchoring bar may measure 6.5 mm and the anchoring bar/linking strip join is offset by about 0.5 mm with respect to the center of the anchoring bar, towards the distal end of the anchoring bar.

The proximal part, or alternatively the distal part, of the stop bar 3 is defined as that part of the stop bar 3 which is located between its proximal end 3b, or alternatively its distal end 3a, and the linking region between the stop bar 3 and the linking strip 4.

In the storage position in the instrument 1, the fastener A is folded so that the linking strip 4 has two curved regions (in the vicinity of its points of attachment to the anchoring bar 2 and the stop bar 3), and a central zone approximately parallel to the bars 2, 3. In this position, illustrated in FIG. 2, the height H of the fastener may be about 5 mm or less. In embodiments, the height of the fastener is no more than 4 mm.

As shown in FIG. 1, the instrument 1 includes a gripping means B to which a tubular body C having a longitudinal axis is fixed. A socket D surrounds the junction region between these two elements. From its proximal end, the tubular body C includes, as will be seen later, a first zone C1 containing a step-by-step system for advancing the fasteners A followed by a second zone C2 in which the fasteners A are stored.

Fixedly mounted on the distal end of the tubular body C is a device 5 for deploying and ejecting the fasteners A, said device projecting beyond the distal end of the tubular body C.

The longitudinal mid-plane of the instrument 1 is defined as the plane passing through the axis of the tubular body C and dividing the gripping means B into two approximately identical parts (corresponding to the plane in which the gripping means B is shown in FIG. 16). The term "transverse" denotes a direction generally perpendicular to this plane, or a plane orthogonal to the longitudinal axis of the tubular body C.

The deployment/ejection device 5 will now be described with reference to FIGS. 3 to 5.

The device 5 has an approximately cylindrical shape, with a diameter of about 5 mm or less. In the example shown, it is formed from a single metal component. In one embodiment the device may be made of plastic and/or formed from several components.

The proximal part of the device 5 forms a cylindrical appendage 6 intended to be introduced into the tubular body C. The distal part 7 of the device 5 has a larger diameter, approximately identical to the outside diameter of the tubular body C, and thus defines a shoulder 8 that butts against the distal end of this body C.

The distal part 7 has the form of a semicylinder bounded by a bearing face 7b which, in the position in which the device 5 is fitted onto the instrument 1, lies generally in the longitudinal mid-plane of the instrument. Thus defined is an open half-space—except upstream—which allows the fastener A to be satisfactorily deployed. The distal end 9 of the device 5 is approximately planar and orthogonal to the longitudinal axis. This distal end 9 of the device 5 may be slightly domed, provided that its mean plane is generally orthogonal to the longitudinal axis of the device 5.

The device 5 includes a first longitudinal channel 10 offset with respect to the longitudinal axis of the device 5. For the sake of simplifying the description, it will be considered hereafter that the first channel 10 is located in the top of the device 5, recognizing that this device 5, once fitted onto the instrument 1, may adopt various positions in space during use.

In the proximal part of the device 5, the first channel 10 has a larger cross section, for reasons that will be explained later. As shown in FIG. 5, which is a sectional view in a plane passing through the longitudinal axis of the device and orthogonal to the longitudinal mid-plane, the junction zone between the proximal and distal parts of the first channel 10 forms a ramp 12 inclined from the proximal end towards the distal end, and towards the axis of the cylindrical distal part of the first channel 10.

The lower zone of the distal part 7 of the device 5 has a shorter length than the first channel 10. This lower zone includes a longitudinal rib 13, lying below the slot 11, substantially along the longitudinal axis of the device 5 and extending substantially from the middle of the distal part 7 right to the distal end of the lower zone. The rib 13 includes a proximal part 14, the proximal face 15 of which forms a ramp a higher distal part 16 of the rib 13 has proximal face 17 which also forms a ramp.

A protuberance 18 on the distal part 16 of the rib 13 extends downwards and has a triangular shape in side view. A proximal face 19 of protuberance 18 is orthogonal to the longitudinal mid-plane and inclined downwards from the proximal end of the device 5 towards the distal end 9. In addition, this proximal face 19 has a concave shape, seen in section in a longitudinal plane orthogonal to the longitudinal mid-plane.

The device 5 further includes a second longitudinal channel 20, offset downwards with respect to the longitudinal axis of the device 5. In the distal part of the device 5, the second channel 20 is opened laterally and defined by a zone 21 set back with respect to the longitudinal mid-plane lying beneath the rib 13. In the proximal part of the device 5, the second channel 20 is approximately cylindrical and joined to the first channel 10 by a longitudinal housing 22 of downwardly elongate cross section.

The device 5 includes a cavity 23 provided in the wall 24 of the first channel 10, in the distal part 7 of the device 5, upstream of the proximal face 15 of the rib 13 and close to the shoulder 8. The cavity 23 has a distal face 25 generally orthogonal to the longitudinal mid-plane.

The description now refers to FIGS. 6 to 15 which show the various phases resulting in the deployment and ejection of a fastener A out of the instrument 1 by means of the device 5, with a view to fixing a prosthesis 26 to human tissue 27.

Referring now to FIGS. 5 to 15 the fasteners A are stored in the tubular body C one behind another with the anchoring bars 2 lying approximately along the axis of the first channel 10 and the stop bars 3 along the axis of the second channel 20 (see FIGS. 5 and 18).

As illustrated in FIG. 5, while the fasteners A are being advanced towards the distal end 9 of the device 5, the end 2c of the anchoring bar 2 of the fastener A furthest downstream butts against the ramp 12 which slides over the latter, thus causing the lateral displacement of said anchoring bar 2 towards the distal part of the first channel 10. The anchoring bar 2 is then pushed towards the distal end 9 of the device 5, in a longitudinal sliding movement in the first channel 10, during which the linking strip 4 slides in the slot 11 and the stop bar 3 is made to slide in the second channel 20.

When the distal end 3a of the stop bar butts against the proximal face 19 of the protuberance 18, which forms a first cam surface (FIG. 6), this distal end 3a slides downwards against the proximal face 19, being guided by the shape of the latter. This pivots the stop bar (FIG. 7) which begins to straighten, while the anchoring bar 2 starts to project from the device 5.

The junction between the linking strip 4 and the stop bar 3 is then in contact with the proximal face 15 of the rib 13, forming a second cam 15 (FIG. 8). Second cam 15 causes a first lateral splaying movement of the proximal part of the stop bar 3, as shown in top view in FIG. 9.

The proximal part of the stop bar 3 then comes into contact with the cavity 23 (FIG. 10). As the sliding of the anchoring bar 2 continues, the distal part of the stop bar 3 continues to slide downwards against the proximal face 19. The angle of pivoting of the stop bar 3 progressively increases and the proximal part of the stop bar 3 cooperates with the distal face 25 of the cavity 23, forming a third cam 25. As a result, the lateral splaying of the proximal part of the stop bar 3 increases (FIG. 11). This lateral splaying allows the stop bar 3 to avoid the lower face of the first channel 10, which would prevent the continuation of the pivoting movement.

Next, the proximal part of the stop bar 3 slides against the wall 24 of the first channel 10 until the distal part of the stop bar 3 comes into contact with the proximal face 17 of the distal part 16 of the rib 13, forming a fourth cam 17 (FIG. 12). This movement results in the lateral displacement of the distal part of the stop bar 3, which escapes from the proximal face 19. The stop bar 3 is then approximately upright (FIG. 13). The continuation of the thrusting movement of the anchoring bar 2 results in it being completely ejected from the device 5 (FIG. 14) and then pivoted, at least through an angle of at least 30° with the linking strip 4 and preferably an angle ranging up to 90° with this linking strip 4. Preferably, the anchoring bar 2 pivots until it is approximately parallel to the upright stop bar 3, which is pressed against the prosthesis 26, the linking strip 4 then being approximately perpendicular to the two bars 2, 3 and the fastener A adopting an upright "I" configuration. In this position (FIG. 15), the fastener A holds the prosthesis 26 against the human tissue 27.

The instrument 1 will now be described in greater detail.

As illustrated in FIG. 16, the gripping means B includes a body 28, made in two symmetrical parts assembled by force-fitting them or by means of rivets or screws, and an actuator 29 mounted so as to move on the body 28 in an articulated fashion about a transverse pin 30 of the body 28, between a pushed-in position and a pushed-out position. A spring 31 urges the actuator 29 towards its pushed-out position.

Housed in the body 29 are the following:

a first control lever 32 articulated to a transverse pin 33 of the body 28, the upper part of said control lever 32 including two projections 34 separated laterally from each other (only one of them being visible in FIG. 16); and a second control lever 35 articulated to a transverse pin 36, housed between the two projections 34 of the first lever 32.

The first lever 32 has a circularly arcuate lower end provided with rack 37 and, in its distal part, with a larger tooth 38. These projections 34 have a cam-shaped distal face 39. Furthermore, the first lever 32 includes, in the central part, a projection 40 capable of cooperating with a transverse lug 41 provided on the second lever 35. The latter includes a cavity, the bottom of which forms a transverse cam 42.

Figure 23:
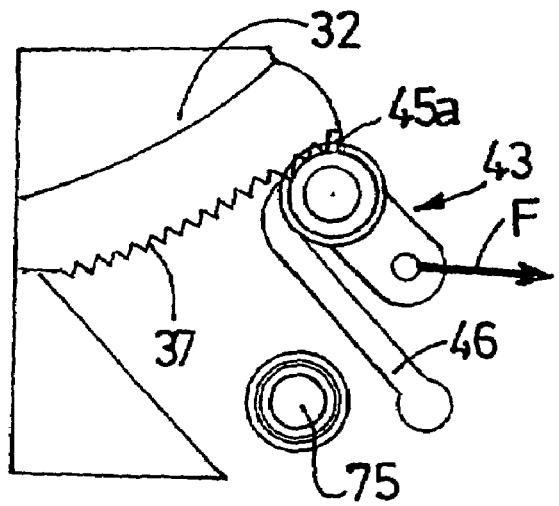
FIGS. 23 and 24 are detailed views of the inside of the gripping means, showing the non-return system of the actuator.
Figure 24:
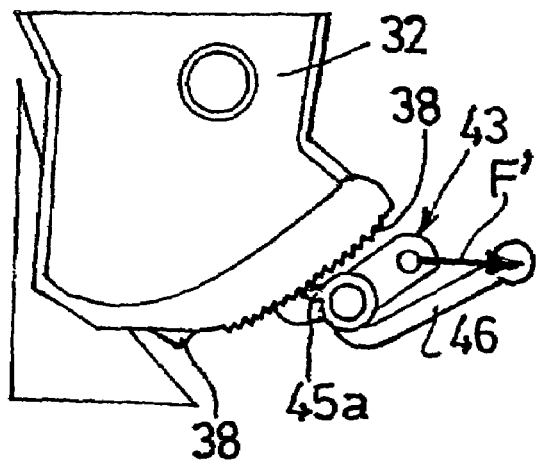

The body 28 of the gripping means B also contains a pivoting member 43 articulated to a transverse pin 44 of the body 28. This pivoting member 43 includes a tooth 45a (visible in FIGS. 23 and 24) capable of cooperating with the rack 37 of the first lever 32, a finger 45, larger than the tooth 45a, and a tab 46 projecting away from the finger 45. A spring 47 links the pivoting member 43 to a transverse pin 48 of the body 28.

The gripping means B is completed, inside the socket D, with a cylindrical ferrule 49 in which, inside a spacer 50, a piston 51 is fitted. The piston 51 has a thinner proximal end part 52, introduced between the two projections 34 of the first lever 32 and, on either side of the proximal end part 52 and distal thereof, two curve surfaces 53 that can cooperate with the cam 39 of the projections 34.

An ejection rod 54 is fixed (for example welded) to the distal end of the piston 51, near its periphery. This rod 54 extends longitudinally, approximately as far as the distal end of the tubular body C. Moreover, the piston 51 has an approximately central longitudinal bore in which an advancing rod 55 can slide. The advancing rod 55 has a proximal end that can cooperate with the cam 42 of the second lever 35 and a curved distal end 56, located in the zone C1 of the tubular body C.

The tubular body C includes a hollow metal envelope 57 (cf. FIG. 19) in which various elements are housed.

Fixedly mounted in the second zone C2 of the tubular body C is a magazine 58 for storing the fasteners A. As illustrated in FIGS. 18 and 19, this magazine 58 comprises a first longitudinal housing 59 that receives the aligned anchoring bars 2 of the fasteners A and, contiguously, the ejection rod 54, a second longitudinal housing 60 that receives the aligned stop bars 3 of the fasteners A, and a third housing 61, which joins the first and second housings 59, 60, for passage of the linking strips 4. These housings 59, 60 and 61 are placed in alignment with the channels 10, 20 and with the housing 22 (cf. FIG. 3) that are provided in the device 5. It should be noted that, in FIG. 18, the ejection rod 54 and the magazine 58 have been truncated in their proximal part in order to make it easier to understand the figure, all the fasteners A being in fact housed in the magazine 58. The magazine 58 may be made in several sections joined together longitudinally.

The first zone C1 of the tubular body C contains a step-by-step advancing system for the fasteners A, which system will now be described with reference to FIGS. 17 to 22.

Component 62 is fixed in the envelope 57 of the tubular body C and is stationary relative to the tubular body C. Component 63, which can move relative to the stationary component 62 is also positioned in the envelope 57. Both these components having the shape of semicylinders superposed along their longitudinal face (FIG. 20).

Provided in the longitudinal face of each of the components 62, 63 are notches 64, arranged with a pitch P approximately equal to the length L of the stop bar 3 of a fastener A. Each notch 64 has an upright transverse proximal edge 65 and a distal edge 66 inclined to the longitudinal axis of the tubular body C towards the periphery of the latter, upon moving away from the distal end of the tubular body C towards this proximal end.

The stationary component 62 has a proximal cylindrical part 67 that defines a transverse stop surface 68. The moving component 63 includes, near its proximal end, a radial orifice 69 into which the curved end 56 of the advancing rod 55 is inserted. In addition, a channel (not shown) is provided in the moving component 63 and in the proximal cylindrical part 67 of the stationary component 62, in order to house the ejection rod 54.

Placed between the longitudinal faces of the stationary component 62 and the moving component 63 is a slide 70, shown in FIG. 17. The slide 70 comprises an approximately planar main part 71, a wider distal part 72 and, in its proximal part, first and second splayed-apart resilient tongues 73, 74. The slide 70 is for example formed from a metal sheet, cut and then folded onto itself, which may be bonded at the main 71 and distal 72 parts, but not at the tongue 73, 74, which are curved away from each other.

Initially, before the first use of the instrument 1, the slide 70 is mounted such that the first tongue 73, projecting towards the moving component 63, is engaged in the proximal notch 64 of component 63, and the second tongue 74, projecting towards the stationary component 62, is engaged in the proximal notch 64 of component 62. The moving component 63 is in contact with the transverse stop surface 68 of the stationary component 62, and the notches 64 of the components 62, 63 face each other in pairs. The distal part 72 of the slide 70 is engaged in the third housing 61 (FIG. 19), bearing against the proximal end 3b of the stop bar 3 of the proximal most fastener A.

The operation of the instrument 1 will now be described.

When a user presses on the actuator 29, it causes the first lever 32 to start to pivot, which, through the cooperation between the projection 40 and the lug 41, results in the second lever 35 pivoting. Through the cooperation between the proximal end of the advancing rod 55 and the cam 42 of the second lever 35, the advancing rod 55 is displaced longitudinally downwards, taking with it the moving component 63, which slides longitudinally relative to the stationary component 62 (FIG. 21). The mechanism is designed so that this displacement corresponds to the pitch P, and therefore to the length L of the stop bar 3 of a fastener A. This value is, for example, about 7 mm.

During this movement, the proximal edge 65 of the proximal notch 64 of the moving component 63 pushes the first tongue 73 downstream. The slide 70 is therefore displaced downstream (the second tongue 74 deforming elastically in order to come into the plane of the main part 71 of the slide 70) and, at the end of the movement, the second tongue 74 is housed in the notch 64 located immediately distal of the proximal notch of the stationary component 62.

The distal part 72 of the slide 70 has therefore pushed the train of fasteners A via the stop bars 3, distally, by the distance P, and therefore the distance L. Consequently, the distalmost fastener A has been displaced in the deployment and ejection device 5, and its anchoring bar 2 has slid over the ramp 12 so as to come into alignment with the ejection rod 54 (FIG. 5).

When the user continues to push in the actuator 29, the second lever 35 remains immobile, as therefore do the advancing rod 55, the moving component 63, the slide 70 and the fasteners A (with the exception of the most downstream one). However, the pivoting of the first lever 32 continues, which, Continued actuation of the actuator 29, through the cooperation between the cams 39 of the projections 34 and the curve surfaces 53 of the piston 51, results in the ejection rod 54 sliding longitudinally downwards. It should be noted that the sliding of the rods 54, 55 is not the same, this being made possible by the fact that the advancing rod 55 slides in the piston 51 to which the ejection rod 54 is fixed.

The distal end of the ejection rod 54 then pushes the anchoring bar 2 of the fastener A located furthest downstream into the deployment/ejection device 5. Via the steps described above (FIGS. 6 to 15), the anchoring bar 2 is ejected into the tissue 27, while the stop bar 3 pivots and the fastener A is deployed. This deployment takes place in the open half-space of the device 5, and therefore outside the tubular body C. The longitudinal travel of the ejection rod 54 is, for example, about 24 mm.

The user can then release the actuator 29. Various elastic return means (not shown) allow the rods 54, 55 to return to their initial positions, awaiting the next time the actuator 29 is pushed in.

When the advancing rod 55 slides proximally, it brings the moving component 63 back against the transverse stop surface 68 of the stationary component 62. However the second tongue 74, in abutment against the proximal edge 65 of the notch 64 of the stationary component 62, prevents the slide 70 from returning further proximal. In FIG. 22, the slide 70 has therefore advanced by one pitch P distally relative to FIG. 20, and it will therefore be able to advance the train of fasteners A distally by one pitch the next time the actuator 29 is pushed in.

Finally, the double non-return system with which the gripping means B is provided will be described with reference to FIGS. 16 and 23 to 27.

Before use, the pivoting member 43 is in the neutral position, as shown in FIG. 16.

When the actuator 29 is pushed in as far as an intermediate position, wherein the tooth 45a of the pivoting member 43 cooperates with the rack 37 of the first lever 32, the spring 47 urges the pivoting member 43 (indicated by the arrow F in FIG. 23) in such a way that the tooth 45a, engaged in the rack 37, prevents the actuator 29 from returning to the pushed-out position from said intermediate position. Thus, the user is forced to continue to press on the actuator in order for the procedure of advancing, deploying and ejecting the fastener A to be completely finished.

Figure 25:
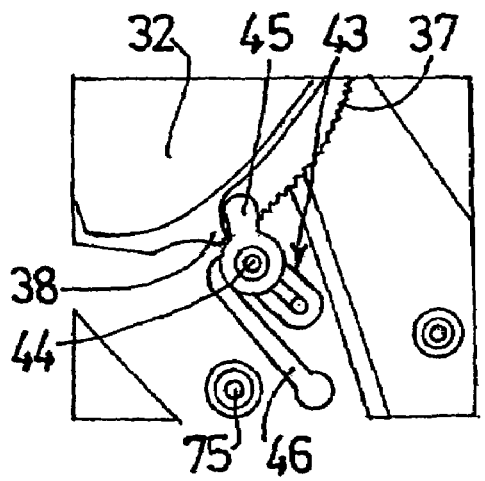
FIGS. 25 to 27 are detailed views of the inside of the gripping means, showing the system for indicating the end of push-in travel of the actuator.
Figure 26:
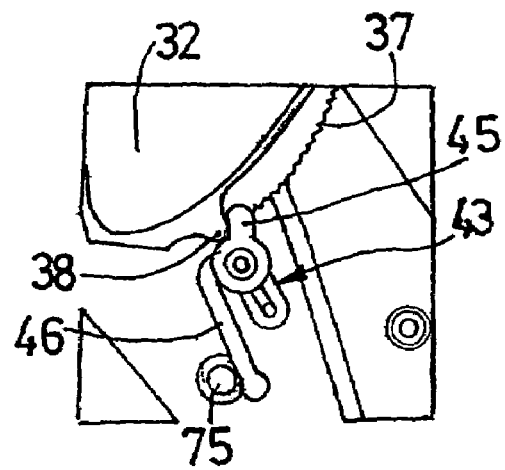
Figure 27:
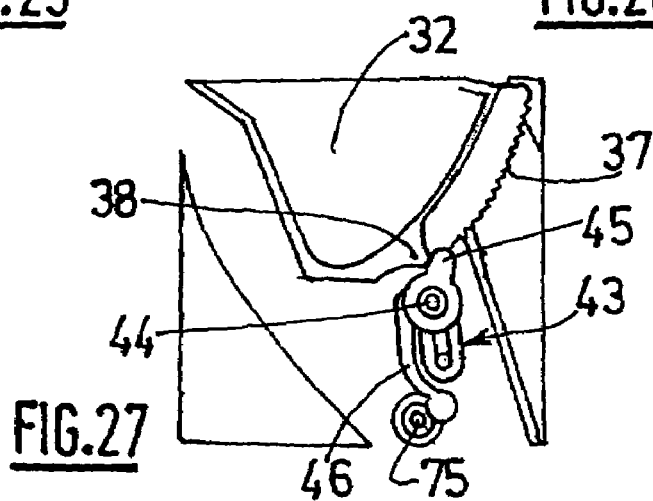

Towards the end of the movement of pushing in the actuator 29, the finger 45 of the pivoting member 43 comes into contact with the larger tooth 38 (FIG. 25). This results in the pivoting member 43 pivoting about its pin 44 until the tab 46 comes into contact with a stop 75 integral with the body 28 of the gripping means B (FIG. 26). An elastic deformation of the tab 46 of the pivoting member 43 in contact with the stop 75 is required for the finger 45 to pass beyond the larger tooth 38 after the actuator has been pushed in (FIG. 27). This constitutes a hard point felt by the user, who can therefore know whether or not the end of travel has been reached and, consequently, whether the fastener A has been correctly ejected. In addition, when the finger 45 passes beyond the larger tooth 38, a sudden pivoting of the first lever 32 takes place, and therefore a sudden advance of the ejection rod 54. This impact is transmitted to the distalmost fastener A which makes it easier to eject and pivot it.

At this step, the pivoting member 43 returns to a neutral position, similar to that shown in FIG. 16, but this time beyond rack 37.

Next, when the actuator 29 is released as far as an intermediate position, the spring 47 urges the pivoting member 43 (indicated by the arrow F' in FIG. 24) in such a way that the tooth 45a, engaged in the rack 37, prevents the actuator 29 from being pushed in from said intermediate position. Thus, the user cannot start a new cycle (advance of the train of fasteners and ejection of the distalmost fastener) until the mechanism has been returned to its rest position. This prevents the mechanism from becoming blocked and guarantees successful ejection of each of the fasteners A.

Figure 29:
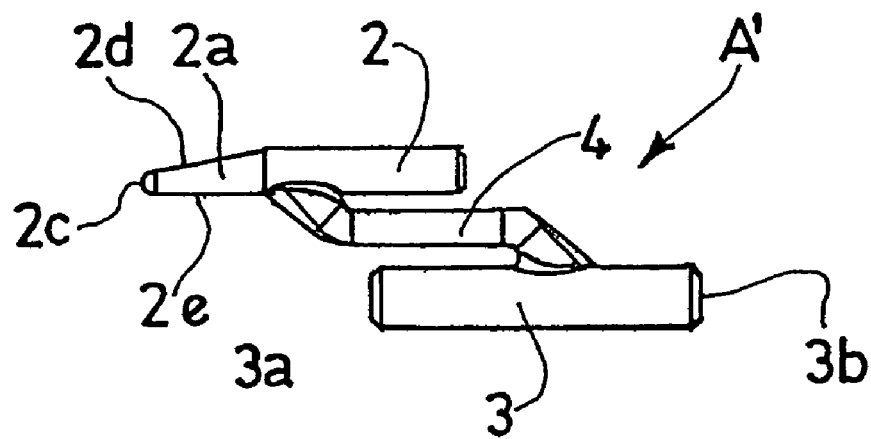
FIG. 29 is a side view of another embodiment of a fastener intended to be ejected and deployed by means of the deployment/ejection device.

Another embodiment of the fastener A' is shown in FIG. 29. Fastener A' has no notch. Fastener A' of FIG. 29 has the general shape of a recumbent "I" in the storage state. The references denoting the same elements as in FIG. 2 have been preserved. The fastener A' comprises an anchoring bar 2 joined to a stop bar 3 via a linking strip 4. The fastener A' may be made of biocompatible and bioresorbable plastic.

The end 2c of the anchoring bar 2 has a hemispherical shape and the distal part 2a of the anchoring bar 2 has approximately the shape of a truncated cone, the external slope 2d of the cone, turned towards the outside of the fastener, being however more accentuated than the internal slope 2e, turned towards the stop bar 3. This accentuation of the external slope 2d of the cone allows the anchoring bar 2 of the fastener A' to pivot more naturally towards the stop bar 3 when the fastener is being positioned in tissue, as shown in FIGS. 13 to 15—pivoting of the fastener A' is thus favored and its deployment towards an upright "I" configuration is thus facilitated.

Figure 28:
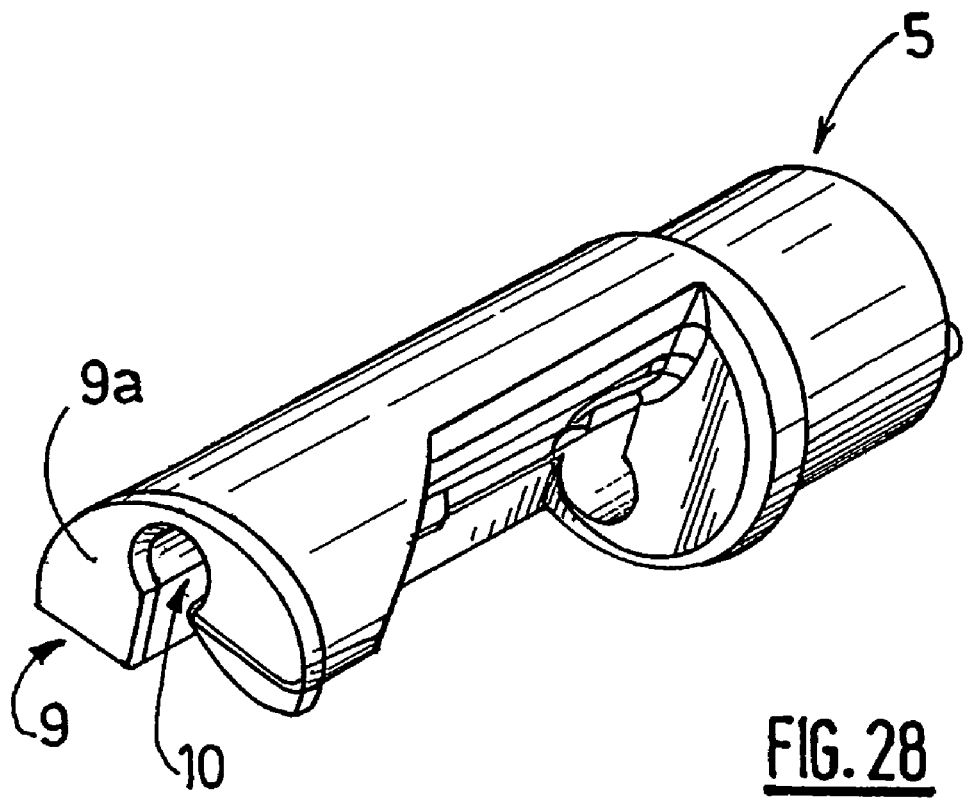
FIG. 28 is a perspective view of an alternative embodiment of the deployment/ejection device.

In the distal part of the device 5, the first channel 10 is approximately cylindrical and has a longitudinal slot 11 opened downwards. This first channel 10 emerges at its distal end near the distal end 9 of the device 5. FIG. 28 shows an alternative embodiment of the device 5 of FIG. 4, in which the distal end 9 of the device 5 includes a transverse wall 9a substantially flanking the distal outlet of the first channel 10. The material added by the presence of this transverse wall 9a provides further protection of the device 5 and minimizes the thrust of the distal end 9 of the device 5 against human tissue when the fastener A is being positioned, for example during the steps shown in FIGS. 6 and 7.

The invention therefore provides a definite improvement over the prior art, by providing a device for deploying and ejecting surgical fasteners and an instrument for storing, dispensing and positioning them that can be used in small-diameter trocars, while still guaranteeing satisfactory deployment of the fasteners and, consequently, very good retention of a prosthesis against human flesh.

The invention is not limited to the embodiment described above by way of example, but on the contrary it encompasses all alternative embodiments thereof.

The invention claimed is:

1. A device for deploying and ejecting a recumbent I-shaped surgical fastener, the fastener having an anchoring bar, a stop bar and a linking strip, the device intended to be positioned adjacent a distal end of an instrument for storing, dispensing and positioning fasteners, the device having a longitudinal axis, a proximal end and a distal end that lies in a first plane approximately orthogonal to the longitudinal axis and includes a first longitudinal channel emerging at the proximal and distal ends of the device, in which the anchoring bar of the fastener can slide longitudinally up to a point where it is ejected at the distal end of the device, the first longitudinal channel having a longitudinal slot intended for passage of the linking strip of the fastener during the sliding, wherein the device has an approximately longitudinal bearing face that defines an open half-space not containing the first longitudinal channel and in that the device further includes:
   a second longitudinal channel in which the stop bar can slide towards the distal end of the device, the second longitudinal channel lying approximately in the first plane, emerging at the proximal end of the device and extending into the open half-space against the bearing face;
   a first cam that closes off the distal end of the second longitudinal channel, designed to form a stop surface for a distal part of the stop bar and to allow sliding from the distal end of the device in the opposite direction to the first channel, so as to produce a pivoting movement of the stop bar;
   at least one approximately transverse splaying cam, located proximal to the first cam, capable of cooperating with the at least one of the linking strip and the stop bar in order to cause a lateral splaying movement of the proximal part of the stop bar away from the bearing face; and
   an approximately transverse escapement cam, located between the first cam and the at least one approximately tranverse splaying cam, capable of cooperating with the distal part of the stop bar in order to allow lateral displacement of the distal part of the stop bar away from the bearing face, and its disengagement from the first cam.

2. A device according to claim 1, wherein the first cam generally lies in a plane orthogonal to the bearing face and is inclined, going away from the first longitudinal channel, from the proximal end of the device towards the distal end.

3. A device according to claim 1, wherein the first cam has, as seen in cross section in a longitudinal plane orthogonal to the bearing face, a concave shape.

4. A device according to one of claim 1, further comprising two approximately transverse splaying cams designed to cause two sequenced lateral splaying movements of a proximal part of the stop bar.

5. A device according to claim 1, further comprising a longitudinal rib projecting approximately at right angles from the bearing face and a proximal face of the longitudinal rib forms a first ramp constituting at least one approximately transverse splaying cam.

6. A device according to claim 5, wherein the longitudinal rib has a proximal part and a distal part which is of greater height than its proximal part, the proximal face of the distal part of the longitudinal rib forming a second ramp which, located downstream of the first ramp, constitutes the approximately transverse escapement cam.

7. A device according to claim 5, further comprising a cavity formed in the bearing face, in line with the first longitudinal channel, upstream of the proximal face of the longitudinal rib, a distal face of which constitutes a second of the at least one approximately transverse splaying cam.

8. A device according to claim 1, wherein the first longitudinal channel has a distal part and a proximal part of larger transverse dimension than the distal part, a side wall of the proximal part of the first longitudinal channel forming a ramp over which a distal end of the anchoring bar of the fastener can slide in order to cause a lateral displacement of the anchoring bar towards the distal part of the first channel.

9. A device according to claim 1 wherein the device has an approximately cylindrical shape, with a diameter less than 6 mm.

10. A device according to claim 9, wherein further comprising a proximal cylindrical appendage of smaller diameter than the device, intended to be inserted into the distal end of an instrument for storing, dispensing and positioning surgical fasteners.

11. A device according to claim 1 wherein the distal end of the device includes a transverse wall substantially flanking a distal outlet of the first longitudinal channel.

12. An instrument for storing, dispensing and positioning I-shaped surgical fasteners, the fasteners having an anchoring bar, a stop bar and a linking strip, the instrument comprising a gripping means provided with an actuator that can move on a body of the gripping means between a pushed-out position and a pushed-in position, an elongate tubular body in which fasteners are stored longitudinally one behind another, which elongate tubular body is fixed to the body of the gripping means, characterized in that it further includes a device for deploying and ejecting a fastener according to claim 1, which device is fixed to a distal end of the elongate tubular body so that the open half-space is located outside the tubular body.

13. An instrument according to claim 12, further comprising:
 a stationary component housed in the elongate tubular body and a moving component housed in the elongate tubular body so that it can be moved in longitudinal translation with respect to the stationary component by means of an advancing rod that can be actuated by the actuator, the stationary component and moving component being placed adjacent a longitudinal face and each having a corresponding notch provided in the longitudinal face, with a pitch corresponding to the length of the stop bar of the fastener; and
 a slide placed between the longitudinal face of the stationary component and moving component, having an approximately plane main part, a distal part that bears against a proximal end of the stop bar of the furthest upstream fastener and, in its proximal end, a first resilient tongue projecting towards the moving component and a second resilient tongue projecting towards the stationary component, each capable of being engaged in the respective corresponding notch,
a geometry of the corresponding notches being designed so that a displacement of the moving component with respect to the stationary component towards a distal end of the instrument causes, thanks to the first resilient tongue engaged in the corresponding notch of the moving component, a displacement of the slide in the same direction, until the second resilient tongue of the slide is engaged in the corresponding notch of the stationary component, and so that a cooperation between the second resilient tongue and the corresponding notch of the stationary component prevents the slide from returning towards a proximal end of the instrument when the moving component is displaced relative to the stationary component towards the proximal end of the instrument.

14. An instrument according to claim 13, wherein the stationary component and moving component have a form of semicylinders, the moving component including a radial orifice into which a curved end of the advancing rod is inserted.

15. An instrument according to claim 12, further comprising, fixedly housed in a distal part of the elongate tubular body, a magazine for storing the fasteners, wherein the magazine includes a first longitudinal housing that receives the anchoring bars of the fasteners and, contiguously, an ejection rod that can be actuated by the actuator, a second longitudinal housing that receives the stop bars of the fasteners, and a third housing, which joins the first and second longitudinal housings, for passage of the linking strips.

16. An instrument according to claim 12, wherein the gripping means comprises:
 first and second levers that can be moved, by pushing in the actuator, between an upstream rest position and a downstream end position, causing a longitudinal displacement in a distal direction of a rod for ejecting the most downstream fastener out of the device and the rod for advancing the fasteners in the elongate tubular body, respectively;
 a member mounted so as to pivot about a pin attached to the body of the gripping means, which member includes a first tooth capable of cooperating with a rack on one of the first and second levers during displacement of the actuator; and
 an elastic return means comprising a first end and a second end, the first end being connected to a pivoting member and the second end being connected to the body of the gripping means, the elastic return means and a profile of the first tooth and of the rack being designed so that:
 when the actuator is pushed in as far as an intermediate pushed-in position, the elastic return means urges the pivoting member towards a position such that the cooperation between the first tooth of the pivoting member and the rack prevents the actuator from returning to the pushed-out position from the intermediate pushed-in position; and
 after the first and second levers have reached their downstream end position, upon releasing the actuator as far as an intermediate release position, the elastic return means urges the pivoting member towards a position such that the cooperation between the tooth of the pivoting member and the rack prevents the actuator from being pushed in from the intermediate release position.

17. An instrument according to claim 16, wherein the rack includes at a distal end, a second tooth of larger size than the first tooth and in that the pivoting member includes, on a first side comprising a finger and, on a second side comprising a tab that is capable of cooperating with a stop attached to the body of the gripping means when the finger comes into contact with the second tooth, so that, when the actuator has been pushed in, an elastic deformation of the tab of the pivoting member in contact with the stop is necessary in order for the finger to pass beyond said second tooth.

* * * * *